United States Patent [19]
Fisher

[11] Patent Number: 5,601,598
[45] Date of Patent: Feb. 11, 1997

[54] TREATMENT DEVICE TO AID IN LONG-TERM CESSATION OF SMOKING

[76] Inventor: Gary R. Fisher, 2251 Federal Ave., Los Angeles, Calif. 90064

[21] Appl. No.: 287,209

[22] Filed: Aug. 8, 1994

Related U.S. Application Data

[63] Continuation-in-part of Ser. No. 902,970, Jun. 23, 1992, Pat. No. 5,501,697.

[51] Int. Cl.⁶ .................................................. A61B 17/00
[52] U.S. Cl. ........................................... 606/204; 131/270
[58] Field of Search ..................................... 606/204, 203, 606/202, 189; 128/898; 131/270

[56] References Cited

U.S. PATENT DOCUMENTS

| | | | |
|---|---|---|---|
| 3,885,576 | 5/1975 | Symmes . | |
| 4,479,495 | 10/1984 | Isaacson | 606/204 |
| 4,590,939 | 5/1986 | Sakowski | 606/204 |
| 4,716,898 | 1/1988 | Chauve et al. | 606/204 |
| 4,997,438 | 3/1991 | Nipper | 606/204 |
| 5,078,728 | 1/1992 | Giarratano | 606/204 |

OTHER PUBLICATIONS

Benowitz, N. (1983) "The Use of Biologic Fluid Samples in Assessing Tobacco Smoke Consumption" in NIDA Research Monograph #; U.S. Department of Health and Human Services. pp. 6–26.

Brown, R. A. and K. M. Emmons (1991) "Behavioral Treatment of Cigarette Dependence" in *The Clinical Management of Nicotine Dependence*. J. A. Cocores, ed.; Springer–Verlag. New York. p. 110.

Glynn, T. and M. Manley. (1976) *National Cancer Institute Manual For Physicians*. U.S. Dept. of Health and Human Services. p. 46.

Kutchins, S. (1991) "The Treatment of Smoking and Nicotine Addiction with Acupuncture" in *The Clinical Management of Nicotine Dependence*. J. A. Cocores, ed.; Springer–Verlag. New York pp. 169–180.

O'Connor, J. and D. Bensky, trans. (1981) *Acupuncture—A Comprehensive Text.*, Eastland Press, Chicago, pp. 243–244.

Powell, J. R. and N. Azrin. (1968) "The Effects of Shock As a Punisher for Cigarette Smoking". *Appl. Behav. Anal.* vol. 1, pp. 63–71.

Smith (1991) "Counterconditioning Methods" in *The Clinical Management of Nicotine Dependence*. J. A. Cocores, ed.; Springer–Verlag. New York pp. 135–149.

Olms (1984) "Increased Success Rate Using 'Tim Mee' Acupuncture Point For Smoking" in *International Journal of Chinese Medicine*, vol. 2, No. 1, Mar., 1985, pp. 33–36.

*Primary Examiner*—Michael Powell Buiz
*Assistant Examiner*—William Lewis
*Attorney, Agent, or Firm*—Henry M. Bissell

[57] ABSTRACT

Removably attachable wrist band devices for use in helping an addicted cigarette smoker permanently quit smoking. The devices comprise an acupressure stimulator section, a wrist attachment section, and an elastic section with controlled elasticity. The wrist band is placed on a user's wrist such that the acupressure stimulator is positioned proximal to the L-7 acupuncture point and the elastic section of the wrist band is positioned on top of the user's wrist. The elastic section of the wrist band is designed to limit the maximal energy that the user can transfer to a unit area of skin when the band is snapped against the wrist. This is so that snapping the wrist band will not be perceived as aversive to the user. The disclosed wrist band devices have the dual functions of providing a non-aversive behavioral modification function together with providing stimulation of the L-7 acupuncture point, which has therapeutic value in treatment of smoking addiction.

17 Claims, 7 Drawing Sheets

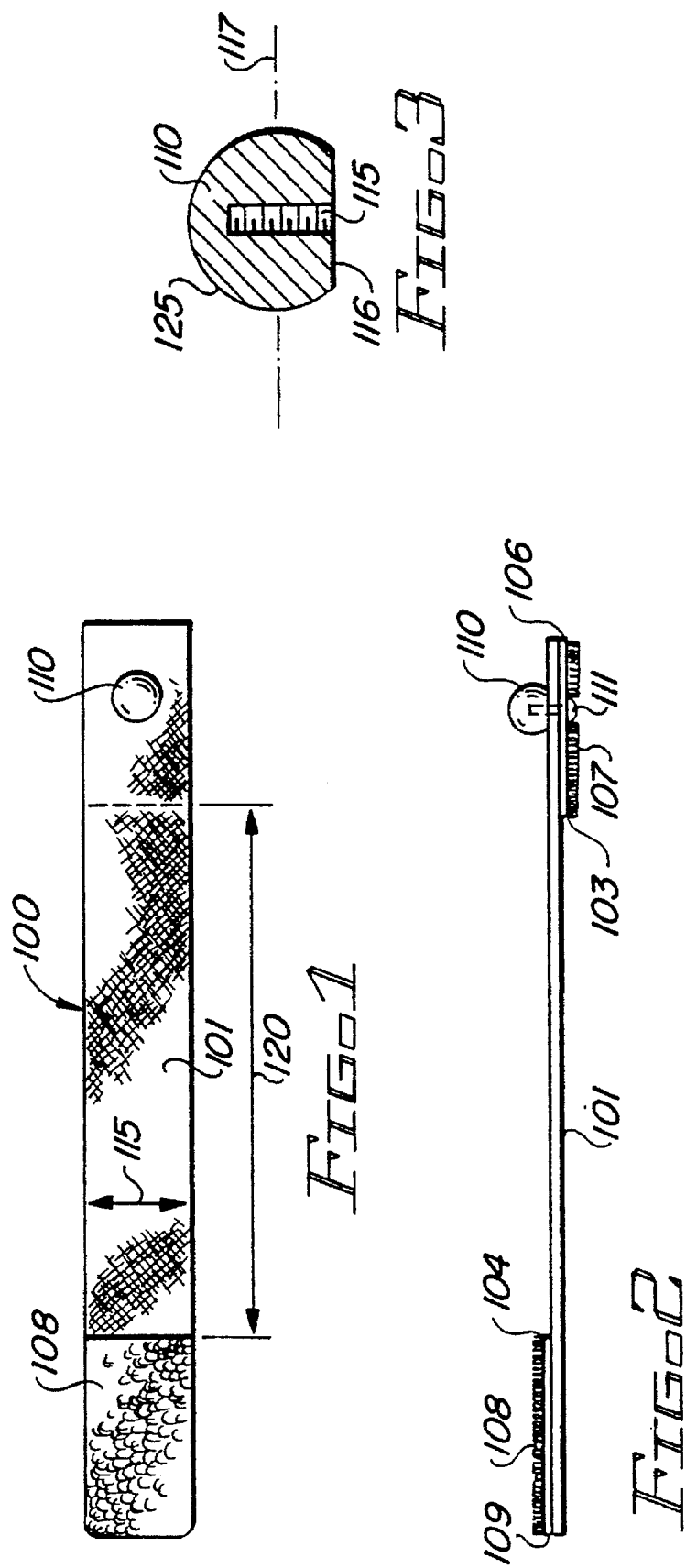

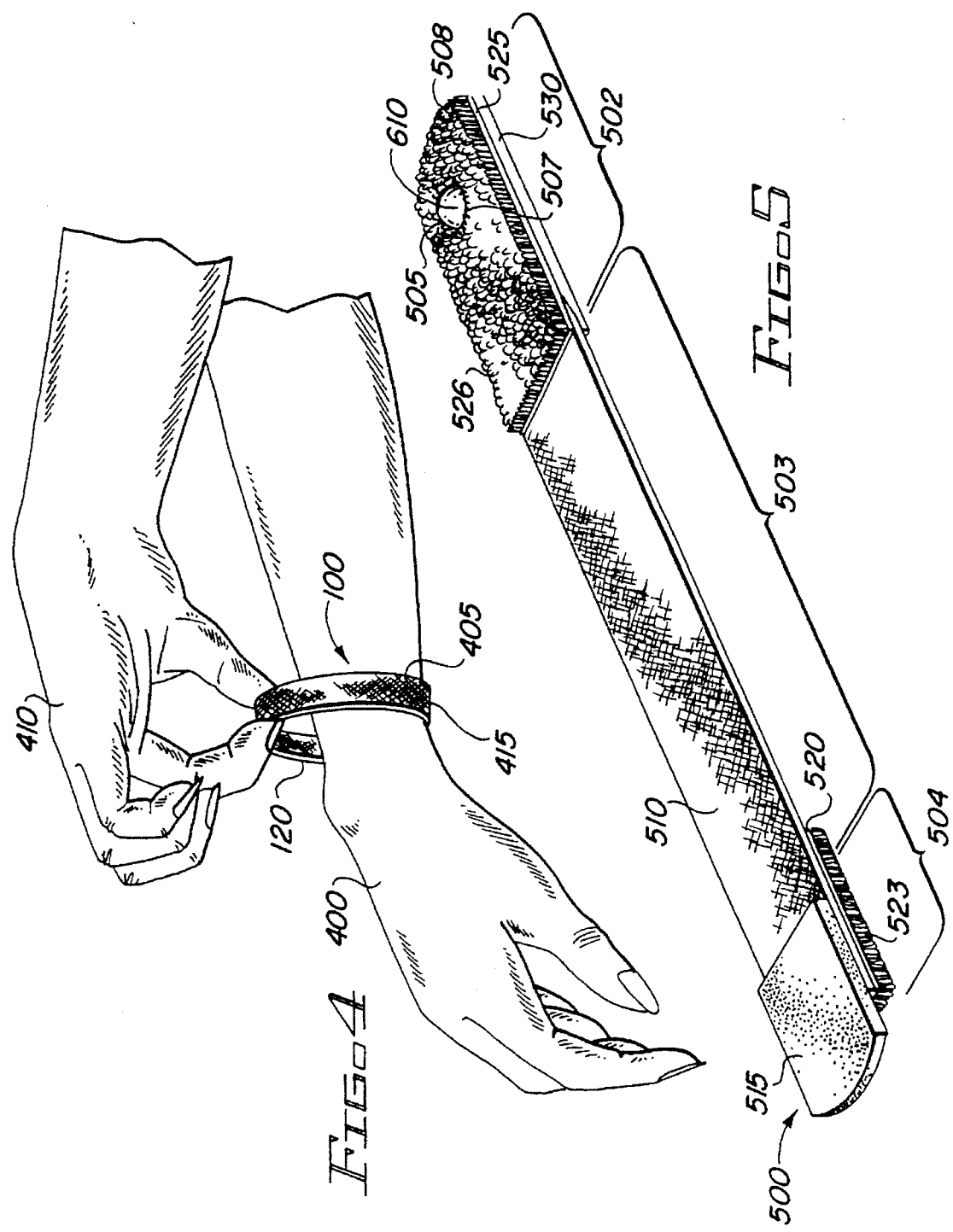

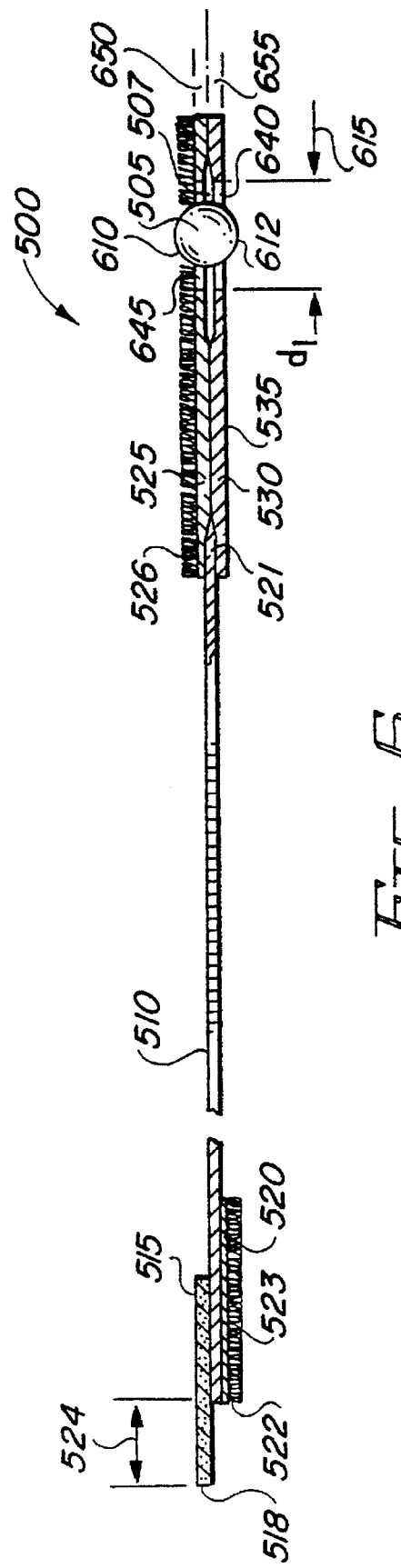

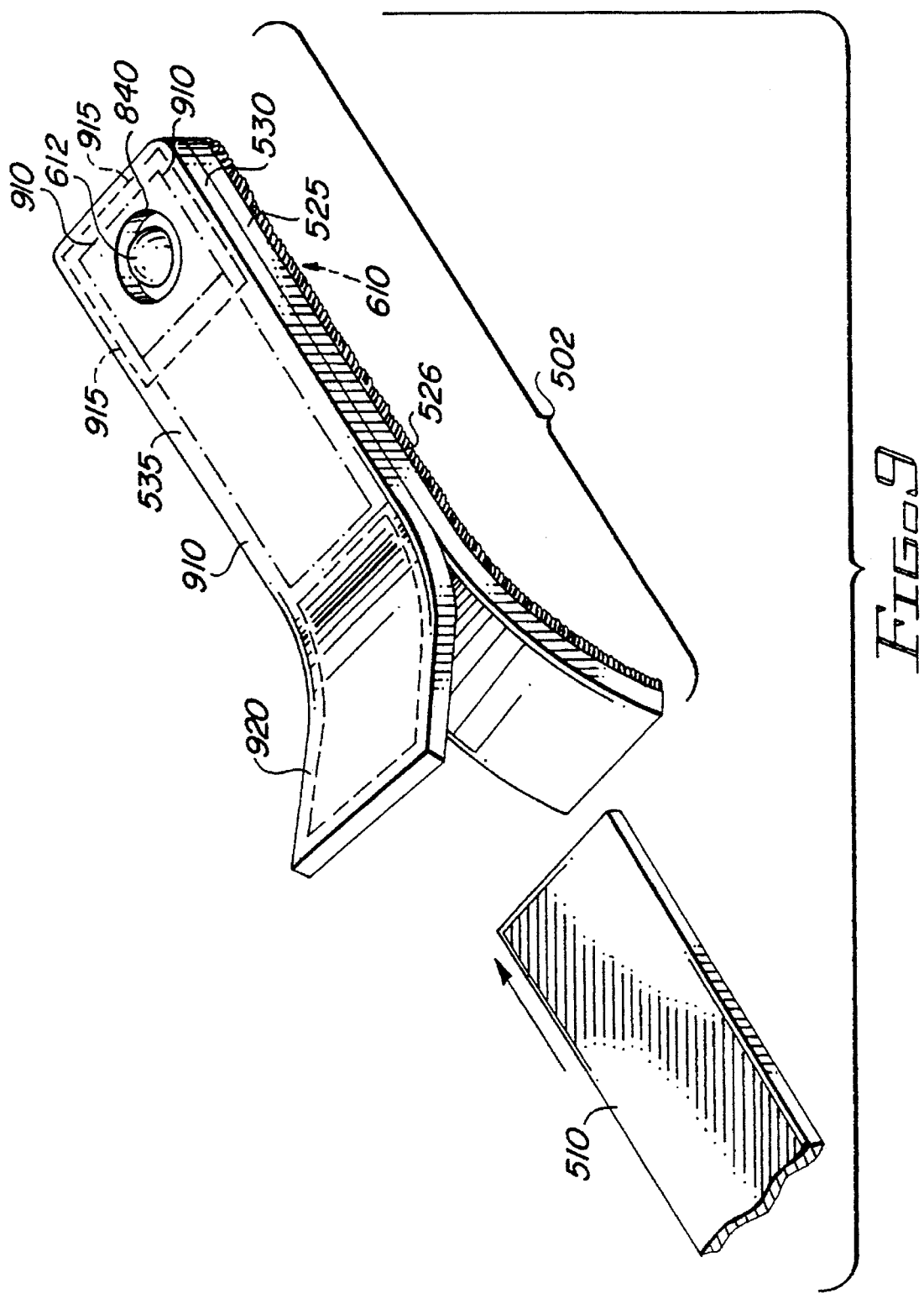

TREATMENT DEVICE TO AID IN LONG-TERM CESSATION OF SMOKING

CROSS-REFERENCE TO RELATED APPLICATION

This application is a Continuation-in-Part of application Ser. No. 07/902,970, filed Jun. 23, 1992, now U.S. Pat. No. 5,501,697.

BACKGROUND OF THE INVENTION

1. Field of the Invention

This invention relates to the fields of psychology and acupuncture and specifically to a device to aid a person in quitting cigarette smoking.

2. Discussion of Related Art

Cigarette smoking is a particularly tenacious addiction. As contrasted to use of illegal drugs, smoking is tolerated in a variety of every day situations. Thus the smoker has the unfortunate opportunity to integrate cigarette usage into virtually every aspect of his daily life.

The addicted smoker develops strong psychological dependencies and habit patterns that remain for many months after nicotine is eliminated from the body. Therefore, quitting smoking is considerably more difficult than simply ridding the body of nicotine.

The physical dependency to nicotine has a strong psychopharmacological basis. Yet surprisingly, nicotine has a half life of just two hours and its principal metabolite, cotinine, has a half life of three to nineteen hours [see Benowitz, N. (1983) "The Use of Biologic Fluid Samples in Assessing Tobacco Smoke Consumption" in NIDA Research Monograph #48; U.S. Department of Health and Human Services. pp. 6–26]. In general, 24 to 48 hours are required for nicotine to be completely eliminated from the body and approximately two weeks for metabolic and other components to be eliminated. Thus, a treatment adjunct that can and will be used for long periods of time after the physical components of the addiction subside is highly desirable.

Most researchers in the field report that the highest success rates for quitting smoking involve the use of a number of treatment modalities. With the exception of dying from cigarette smoking related causes, there is no sure-fire single method of quitting smoking.

Pharmacological adjuncts have been employed to treat the physical addiction to nicotine. Among these, nicotine polacrilex (gum) has been used in several clinical and self-management programs. In terms of the gum's efficacy, Brown and Emmons (1991) report that "it may be more effective in increasing short-term abstinence, rather than long term outcome." [Brown, R. A. and K. M. Emmons (1991). "Behavioral Treatment of Cigarette Dependence" in *The Clinical Management of Nicotine Dependence*. J. A. Cocores, ed.; Springer-Verlag. New York. p.110]. Recent research has demonstrated that a similar argument could be made for the nicotine "patch" if on-going behavioral modification is not incorporated as a treatment adjunct.

A review of a variety of aversion therapy techniques is given by Smith (1991) [in *The Clinical Management of Nicotine Dependence*. J. A. Cocores, ed.; Springer-Verlag. New York pp. 135–149]. Among short term techniques that have been used are focused smoking, rapid smoking, taste aversion, faradic (electric) shock, and covert sensitization. In general, these techniques have been employed during and immediately after the period in which the smoker is still physically addicted to nicotine and with the possible exception of covert sensitization are not appropriate for use on a long-term basis. Faradic shock has been employed in a number of clinical treatments and is a part of the short-term treatment paradigm used by the Schick Center. Symmes, [U.S. Pat. No. 3,885,576], disclosed a device comprising a wrist band with a mercury switch that induces an electric shock when the user raises his hand to (ostensibly) bring a cigarette to his lips. This and other conceptually similar devices have an inherent drawback when used to curb cigarette addiction. For example, Powell and Azrin (1968) in a study of self-administered electric shock to limit cigarette intake, found that the greater the shock intensity the less time the subjects tended to use the device [Powell, J. R. and N. Azrin. (1968) *Appl. Behav. Anal.* Vol 1, p.63–71]. The authors concluded that the subjects developed an aversion to the shock technique itself, which would suggest a limitation to its long term utility. In other words, it is doubtful that users would employ such a device on a self-administered basis after the physical dependency stage of cigarette addiction is over.

Use of a wrist-worn rubber band has been suggested by Glynn and Manley (1976) as one of a number of behavioral-modification techniques to aid smokers in quitting [Glynn, T. and M. Manley. (1976) *National Cancer Institute Manual For Physicians*. U.S. Dept. of Health and Human Services. p.46]. The authors suggest that the band be snapped each time the smoker wants a cigarette and be accompanied by the smoker imagining a stop sign and repeating the word "stop" in his mind.

The foremost drawback of a wrist-worn rubber band for curbing cigarette addiction is that a rubber band is highly extensible and therefore the user can self-inflict considerable pain and erythema depending upon how aggressively he "snaps" the band. As the research of Powell and Azrin suggests, the user may very likely develop an aversion to the rubber band's "sting" and cease its use. On the other hand a wrist band especially designed to limit the maximum "sting" to an acceptably low level may very well enhance the "snap" technique's efficacy for long-term behavior modification due to its acting as an associative agent rather than an aversive therapy device.

Another drawback to the use of a wrist-worn rubber band as described above is that the rubber band has low face validity to the user as a treatment device. The very fact that the band has ubiquitous uses and is essentially cost-free, may lower its perceived potential effectiveness in the user's mind.

A third drawback of the wrist-worn rubber band is that it is not adjustable.

Acupuncture has been used to treat a variety of drug dependencies including cigarette addiction. For treatment of nicotine addiction Kutchins (1991) prescribes stimulation of the L-7 (Lieque) acupuncture point (proximal to the wrist crease) and lung points of the ear [Kutchins, S. (1991) "The Treatment of Smoking and Nicotine Addiction with Acupuncture" in *The Clinical Management of Nicotine Dependence*. J. A. Cocores, ed.; Springer-Verlag. New York pp. 169–180]. He reports that in some cases stimulation of L-7 alone is sufficient in that stimulation of the lung points of the ear tend to replicate L-7 in treatment of the addiction. As with more traditional approaches, Kutchins recommends that acupuncture be a part of a multi-faceted approach to treatment. Kutchins reports that use of acupuncture is efficacious and supported by clinical evidence—especially in the short term context.

Olms (1984) reports the use of the "Tim Mee" acupuncture point for the treatment of smoking addiction. This point is located proximal to L-7 but more dorsally on the wrist. Olms reports that stimulation of the Tim Mee point reduces the desire to smoke and suppresses coughing. [Olms, J. (1985). *Intl. J. Chinese Medicine*, 2:2, pp 33–36.].

Isaacson [U.S. Pat. No. 4,479,495] discloses an acupressure point stimulator mounted to an adjustable strap for use in stimulating acupuncture points on the limbs. In use, an appropriate stimulator is positioned over the desired acupuncture point and the strap tightened so as to exert force on the region of the desired point. When used on a lower extremity, limb movement (for instance, walking) provides constant and differential stimulation to the chosen point. However, if the device is used on the lower arm, no such differential stimulation will occur during normal arm movement.

It should be noted that the L-7 acupuncture point (and to a lesser degree, the Tim Mee point) is located proximal to the radial artery, cephalic vein and various nerves. It is therefore prudent that a strong continuous force against the L-7 region be avoided. Such reasoning would argue against a device (such as in Isaacson) that is intended to be purposely cinched down so as to specifically apply constant force against the L-7 region.

What is needed is a device which is simple and economical to fabricate and to use, is not subject to the disadvantages mentioned hereinabove with respect to the prior art approaches to solving the problem, and which is effective as an aid to breaking the smoking habit. The present invention combines the treatment modalities of a "snappable" wrist band with limited "sting potential" and an L-7 acupuncture point stimulator. This treatment combination is advantageously made possible by the proximity of acupuncture point L-7 to the wrist crease. To the extent that the Tim Mee acupuncture point is an effective alternative to L-7 and in light of the proximity of the Tim Mee point to L-7, the embodiments disclosed herein apply to the Tim Mee point as well.

SUMMARY OF THE INVENTION

The invention provides removably attachable wrist bands for use in helping an addicted cigarette smoker permanently quit smoking.

The wrist bands of the present invention are adjustable so that they can fit a range of wrist circumferences. Hook and loop fasteners are employed for securing the bands around the wrist Advantageously, the hook and loop fasteners resist the shear force generated when the wrist bands are stretched prior to release.

The elastic portion of the bands is designed to limit the band's "sting potential", thus taking the device out of the realm of classical aversion therapy and further reducing the likelihood of users developing an aversion to the device for long term use.

The present invention provides differential stimulation of L-7 when the elastic portion of the band is stretched or when the band is pressed in the region of the stimulator.

Snapping the band acts as an on-going association technique for the smoker to become consciously aware of the context in which he desires each cigarette. This helps the smoker confront the pervasiveness of the habituation and psychological dimensions of his addiction. Further, by forming a mental image of being "smoke-free" each time the band is snapped and the desire to smoke arises, the smoker re-enforces his decision to quit. Importantly, the bands of the present invention can be worn and used for many months, thus reducing the possibility of recidivism.

In the first embodiment of the invention, the wrist band comprises an elastic section, a hook fastener section, a loop fastener section, and an L-7 acupressure stimulator operatively attached to the loop fastener section of the wrist band.

The wrist band is made adjustable by use of hook and loop fasteners which advantageously resist the shear force generated when the band is used according to the invention.

The wrist band is attached to the user's wrist such that the acupressure stimulator is positioned proximal to the L-7 acupuncture point and the elastic section of the wrist band is positioned on top of the user's wrist. The maximal energy transferable by the wrist band to a unit area of skin, when the band is stretched and released, is controlled by both the width of the wrist band and its elastic composition. By constraining this maximal energy to a level wherein the maximum "sting" the user can self-inflict is non-aversive, the user is prevented from developing an aversion to the wrist band.

Snapping the wrist band has the dual functions of providing the user with associative techniques for confronting the habit and psychological components of his addiction, and providing differential stimulation of the L-7 acupressure point, which has therapeutic value in treatment of smoking addiction.

In the second embodiment of the invention, the wrist band comprises an elastic section, a non-elastic wrist attachment section, and a non-elastic stimulator section. The wrist attachment section is comprised of two strips, a wrist attachment tab strip and a fastening strip. The tab strip facilitates removal of the wrist band after use. The fastening strip has a hook-attachment surface for meshing with a mating surface on the stimulator section.

The stimulator section is comprised of a stimulator element captured between two opposed strips, a retaining strip and a fastening strip, respectively. The fastening strip has a loop-fastener surface to mesh with the hook-attachment surface of the wrist attachment section.

In one arrangement of the second embodiment the stimulator element is comprised of two opposing protrusions and a medially disposed flexible, deformable membrane. The protrusions and membrane communicate with openings in the fastening and retaining strips of the stimulator section in such manner that force applied to one protrusion causes deformation of the membrane and concomitant transfer of force to a skin surface proximal to the tip of the second protrusion. The stimulator element is non-removably fastened between the two strips in the stimulator section of the wrist band.

When used for L-7 stimulation, the preferred embodiment of the invention minimizes or eliminates pressure in the immediate region of the L-7 acupuncture point unless the wrist band is purposely snapped or force is applied to the stimulator protrusion. This tends to eliminate discomfort which might occur in some users if constant pressure proximal to L-7 were applied. Additionally, the distensibility of the membrane of the stimulator element, during use, compensates for slight departures from proper placement of the wrist band by the wearer. Furthermore, the opposing protrusions provide the user with a physical cue for aligning the stimulator element over L-7.

In another arrangement of the second embodiment, the stimulator element is comprised of two opposing protrusions and a medially disposed membrane, wherein the membrane is composed of two segments. The first segment, proximal to the protrusions, acts similarly to the deformable membrane of the first stimulator element embodiment; the second, distal to the protrusions, acts as a detachment segment.

The stimulator element is captured between the fastening and retaining strips of the stimulator section at the detachment segment of the membrane. When permanent removal of the stimulator protrusions is desired, the protrusions may be forcibly pushed through the openings in the retaining and fastening strips of the stimulator section until the detachable membrane tears at its boundary with the deformable membrane. Permanent removal of the stimulator protrusions would be indicated if acupressure therapy is to be confined only to the physical withdrawal stage of smoking cessation.

BRIEF DESCRIPTION OF DRAWINGS

A better understanding of the present invention may be realized from a consideration of the following detailed description, taken in conjunction with the accompanying drawings in which:

FIG. 1 is a top view of the wrist band portion of one arrangement in accordance with the present invention;

FIG. 2 is a side view of the wrist band of FIG. 1;

FIG. 3 is a side sectional view of an acupressure stimulator element of the arrangement of FIG. 1;

FIG. 4 is a perspective view of the wrist band of FIG. 1 shown in place on a user's right wrist with the stimulator element positioned over acupuncture point L-7 and illustrating the band in stretched position prior to release;

FIG. 5 is a perspective view of a second embodiment of a wrist band and stimulator element of the present invention with the skin-side of the band facing downward;

FIG. 6 is a side sectional view of the wrist band in FIG. 5, where the section is taken parallel to the length of the band and through the center of the stimulator element;

FIG. 9 is a perspective view of the stimulator segment of the wrist band in FIG. 5 prior to attachment of the elastic segment, where the view is taken from the skin side of the stimulator segment of the wrist band.

DESCRIPTION OF THE PREFERRED EMBODIMENTS

Figure 7B:
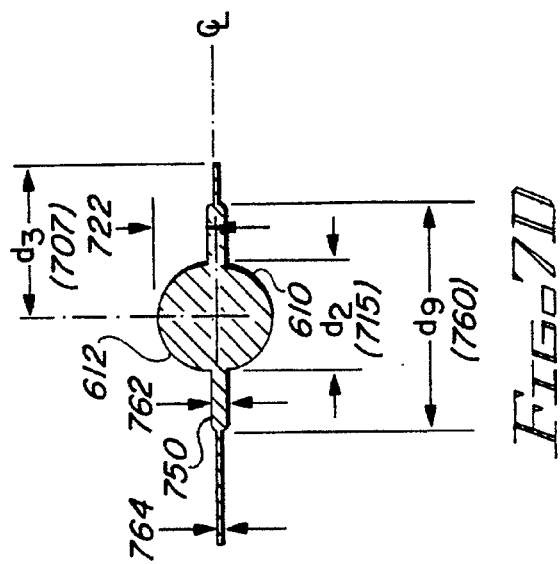
FIG. 7B is a side view of the stimulator element in FIG. 7A at twice scale.

While the male personal pronoun is employed in the description to follow, it should be understood that the devices disclosed herein are intended for both males and females. First Embodiment.

FIGS. 1 and 2 are top and side views, respectively, of wrist band 100. The wrist band comprises elastic section 101, loop fastener section 103, hook fastener section 104, and acupressure stimulator 110.

Loop fastener section 103 is comprised of a plurality of loops 107 operatively attached to a flexible non-elastic backing 106. Backing 106 is attached to elastic section 101 as shown in FIGS. 1–2. Backing 106 can be physically attached by adhesive, stitching or equivalent means.

Hook fastener section 104 is comprised of a plurality of plastic hooks 108 operatively attached to flexible non-elastic backing 109. Backing 109 is attached to elastic section 101 at location 109 by adhesive, stitching or equivalent means. Hook and loop fastener sections 103,104 are adapted to mutually engage each other on contact and are preferably Velcro (tm).

By reference to FIG. 2, hook section 104 and loop section 103 are shown attached on opposite ends and on opposing sides of elastic section 101. The purpose of this orientation is to allow wrist band 100 to be removably attachable to a human wrist. Advantageously, the hook and loop fastener sections allow wrist band 100 to fit a broad range of wrist sizes. Additionally, hooks 108 and loops 107, when engaged, effectively resist the shear force generated by stretching elastic section 120 (FIG. 1) when wrist band 100 is used as intended with this invention.

Elastic section 101 is comprised of an elastic fabric preferably of braided polyester and rubber. Alternatively, an organic fiber may be substituted for the polyester to the extent that it enhances the comfort, breathability, and moisture-wicking of the composite. Since hook fastener section 104 and loop fastener section 103 are intimately attached to elastic section 101, only section 120 of the wrist band in FIG. 1 is capable of extensibility.

In order to limit the maximum "sting potential" of the wrist band to a level below which it will be perceived as aversive, the maximal energy that can be transferred by "snapping" the band to a unit area of skin must be limited. This requires that the maximum elongation of the wrist band, its width, and the force required to attain maximum elongation be determined on an empirical basis.

To meet this requirement a number of elastic fabrics were tested. It was found that polyester/rubber braided fabrics with a maximum elongation of 100%, a width between 0.5 inches and 1.0 inches, and a tensile force of five pounds to attain maximum elongation were conservatively perceived to be non-aversive. Further, with these values no erythema was observed after repeated "snaps".

One suitable elastic fabric meeting the above criteria is manufactured by Rhode Island Textile Company [Stretchrite Elastic (R) #SS34]. This is a ¾" wide longitudinally braided fabric containing 69% polyester and 31% rubber.

Since the inventor has an average threshold of pain and since pain thresholds vary with different individuals, the above values were intentionally chosen to be in the less-aversive rather than more-aversive region. It should be noted that the combination of fabric width, fabric composition and weaving, maximum extensibility, and the force required for maximum extensibility that will yield a band judged non-aversive, may differ for different user populations. In practice, this might dictate using elastic sections with different, empirically determined properties for each of the different populations.

FIG. 2 shows acupressure stimulator 110 attached to elastic section 101 by means of screw 111.

The purpose of stimulator 110 is to stimulate acupuncture point L-7 when wrist band 100 is wrapped around the user's wrist, with 110 in contact with the skin surface immediately over the L-7 acupuncture point, and the wrist band is used according to this invention. The location of L-7 is described in *Acupuncture—A Comprehensive Text*, [Eastland Press, Chicago; J. O'Connor & D. Bensky, trans. (1981) p.243–244] as being proximal to the styloid process of the radius, above the wrist crease in a small hollow and anatomically between the tendons of the brachioradialis and the abductor pollicis longus muscles. The drawing on page 244 of the text illustrates how the opposing hand can be employed to easily locate the hollow. Advantageously, differential stimulation of L-7 arises each time the band is stretched or when the user presses the wrist band proximal to stimulator 110.

A side sectional view of stimulator 110 is shown in FIG. 3. Recess 115 is tapped to receive screw 111. As shown in FIG. 2, elastic section 101 and loop fastener section 103 are bored to receive screw 111. This allows choice of different stimulators to be removably applied to wrist band 100 depending, for instance, on the anatomical and osteological development of a particular user and on the length of time from smoking cessation. Although not shown in FIG. 3, recess 115 could alternatively be bored to receive a press-fit rivet. This would be indicated if a single non-removable acupressure stimulator were to be used during the entire treatment period.

The surface of stimulator 110 is described at least partially by a generally curved surface 125 and a generally flat truncation surface 116 for mating with wrist band 100. For illustrative purposes, the shape shown for the stimulator in FIG. 3 is a truncated sphere although ellipsoidal, parabolic, or other mathematical forms could alternatively be specified.

In FIG. 3 the truncated sphere is illustrated with truncation plane 116 below an imaginary plane 117 bisecting the sphere at its diameter. The stimulator, truncated at this plane allows a user more control in effectively concentrating force in the region of the desired acupuncture point L-7 by the application of concentrated or rolling force from the direction of loop fastener section 103 of the wrist band. This might be an appropriate configuration for use immediately after smoking cessation. Alternatively, a truncation plane 116 chosen closer to 117 will reduce the level of differential stimulation and control when force is applied as described above. This plane might be appropriate for a stimulator employed after physical addiction is quelled.

Stimulator 110 can be of plastic or rubber. Suitable plastics include acrylic or styrene. Suitable rubbers include natural rubber or a synthetic such as silicone or butyrate.

It should be noted that while not shown in FIG. 3, a soft rubber stimulator would require a tapped insert at 115 in body 110 to allow screw 111 in FIG. 2 to be used.

In practice a hard plastic stimulator (such as acrylic) could be employed during the early stages of smoking cessation. This would allow more concentrated force to be applied to the region of L-7. During this period a stimulator with a truncation 21. point 116 as indicated in FIG. 3 would further allow the user finer control of acupressure force.

As the length of time from smoking cessation increases. and depending on the smoker's diminishing desire to smoke increasingly compliant stimulators could be used with the wrist band. These would provide successively lower levels of differential stimulation when the wrist band is snapped.

The method by which a user attaches wrist band 100 to his wrist will now be described. While the band can be used on either wrist, for descriptive purposes attachment to the right wrist shall be described.

The user holds wrist band 100 proximal to 110 in his left hand and locates L-7 on his right wrist. Stimulator 110 is lightly pressed into the L-7 hollow and held in place with the thumb of the left hand while the band is simultaneously wrapped around the wrist and secured with fasteners 107 and 108. In the preferred position extensible elastic section 120 is oriented on top of the wrist. The band should be adjusted such that slight pressure is felt in the wrist hollow; this pressure should be just sufficient to keep the band from shifting appreciably in normal use. The band should not be adjusted so tightly that it interferes with circulation.

FIG. 4 illustrates a side perspective view of wrist band 100 attached to a user's right wrist 400 and stretched in region 120 by the thumb and index finger of the user's left hand 410 into stretched state prior to release. The position 415 of acupressure stimulator 110 is located above L-7 acupuncture point 405. In this stretched state stimulator 110 exerts a differential pressure on the region of L-7 relative to the band's pre-stretched state. This has an efficacious effect on L-7 stimulation.

As has been described earlier, the wrist band according to this invention limits the energy that the user can transfer to a unit area of skin, thus limiting what has been called the "sting potential" of the band. By limiting the "sting potential" of the band, development of user aversion to the device is minimized.

In using the wrist band according to this invention the user stretches wrist band 100 in region 120, as shown in FIG. 4, each time the desire to smoke arises. The band is then released, whereby it snaps against the wrist. The act of snapping the band should be accompanied with positive awareness of the context in which the cigarette was desired, coupled with a user-specific mental image of being "smoke-free". This mental image can either be positive or negative.

On one level, the act of snapping the wrist band acts as a simple replacement for the act of smoking. On another level, the recovering smoker—over time—replaces the desire to smoke with the associations made during the process of snapping the band. On a further level, the band helps the smoker confront the psychological and habituation dimensions of his addiction each time the desire to smoke arises. The wrist band of this invention thereby aids the committed recovering smoker in modifying his behavior.

As stated earlier, differential stimulation of L-7 occurs each time the band is snapped thus providing therapeutic value in addition to the band's behavioral modification benefits. To heighten such stimulation, especially in the early stage of smoking cessation, it may be advantageous to apply pressure using the thumb or one of the fingers of the opposing hand to the region of the stimulator for several seconds immediately after the band is snapped.

When the desire to smoke arises in situations where the act of snapping the wrist band may be socially obtrusive, the use: may alternatively apply constant or rotational force to the wrist band proximal to the stimulator. This should be accompanied with the user imagining that he is snapping the wrist band together wit enacting the mental imagery described above.

Second Embodiment.

It should be noted that with the wrist band shown in FIGS. 1–4, a certain amount of constant stimulation to the region of L-7 always attains if the wrist band is adjusted as described above. For non-compliant stimulators 110, this stimulation will be more intense than if a soft stimulator is specified. For some users, for instance those without significant padding in the region of L-7, discomfort might be experienced if the band is worn for long periods. This might lead to disuse of the band or removal of the acupressure stimulator before withdrawal symptoms have subsided. For this reason and for additional grounds that will become apparent in light of the following discussion, a second embodiment of the invention will now be disclosed. Among other features, this embodiment minimizes or eliminates stimulation of the region proximal to L-7 unless stimulation is purposefully initiated by the user.

FIG. 5 shows a perspective view of the alternative embodiment of the wrist band and stimulator element. FIG. 6 shows a side sectional view of the alternative embodiment of the wrist band 500 depicted in FIG. 5. The section is taken parallel to the length of the wrist band and through the center of the stimulator element.

The wrist band 500 is comprised of three segments, a non-elastic stimulator segment 502, a limited-elasticity, elastic segment 503, and a non-elastic wrist attachment segment 504. Each of these segments of the wrist band shall be described briefly and then in more detail.

The stimulator segment 502 of the wrist band is comprised of stimulator element 505, fastening strip 525, and skin-side stimulator retaining strip 530. Fastening strip 525 is preferably loop-type Velcro material with the loop surface 526 disposed a: shown in FIG. 6. The outside surface 535 of stimulator retaining strip 530, which is placed against the wrist during use, is preferably non-abrasive. While not shown in the figures, loop-type Velcro can be specified for strip 530 owing to the breathability of the loop structure and its non-abrasive nature; further, strip 530 can be of a different color than strip 525 to aid the user in placing the correct side of the wrist band against the wrist prior to use. The thickness of strip 530 is preferably approximately equal to the thickness of strip 525.

Stimulator element 505 proximal to end 508 of segment 502 is captured in place between strips 525 and 530; similarly, elastic strip 510 at its proximal end 521 is captured at the distal end of strips 525 and 530 as shown in FIG. 6. The preferred method of fastening these respective elements securely in their desired orientation and position is by stitching. Alternative fastening means include adhesive and ultra-sonic welding.

Limited-elasticity elastic segment 503 is comprised of strip 510 of elastic fabric with the elastic properties chosen so that "snapping" the wrist band will be judged to be non-aversive by those in the intended user population. The properties of elastic segment 503 include: fabric width, fabric composition and weaving, maximum extensibility, and the force required for maximum extensibility.

The non-elastic wrist attachment segment 504 of the wrist band 500 is comprised of wrist attachment tab strip 515 and fastening strip 520. Tab strip 515 is preferably a tight-weave fabric, pliable leather, or flexible vinyl. The surface 523 of fastening strip 520 is preferably hook-type Velcro. When the wrist band is attached to a user's wrist according to this invention, the Velcro hook-type surface 523 of strip 520 meshes with the loop-type surface 526 of strip 525 to secure the wrist band on the wrist.

As shown in FIG. 6, the distal end 522 of elastic strip 510 is sandwiched between strips 515 and 520 such that the distal termination of strip 520 is essentially coincident with the distal termination of strip 510. The distal termination 518 of tab strip 515 purposely extends a distance 524 beyond the distal terminations of strips 510 and 520. This extension serves as a finger grip to aid in removing the wrist band after use. Extension distance 524 is preferably of the order of 0.25". Strips 510, 515, and 520 are preferably securely joined by stitching or other fastening means.

Figure 7D:
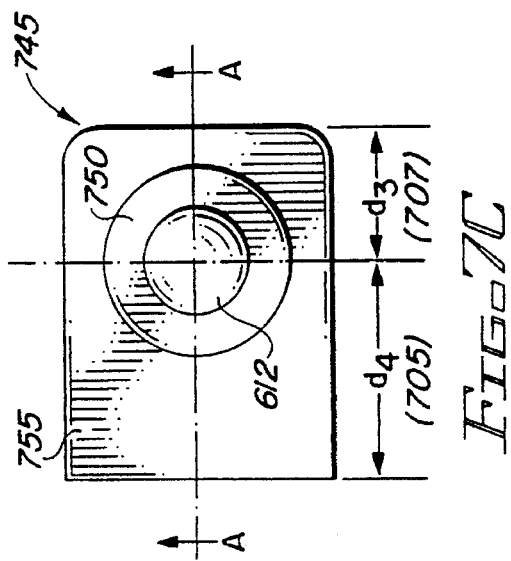
FIG. 7D is a side sectional view of the stimulator element in FIG. 7C at twice scale, with the thickness of the membranes further exaggerated.
Figure 7A:
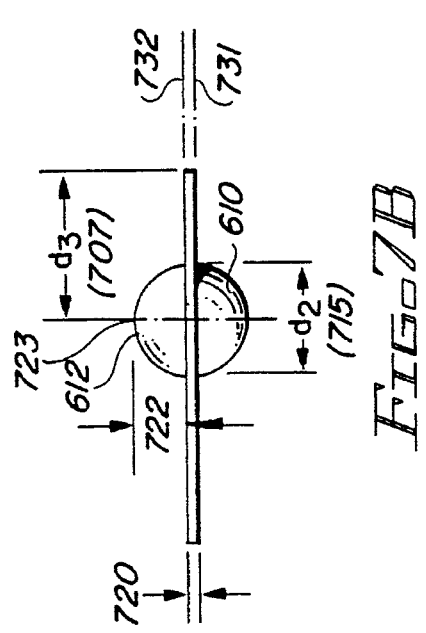
FIG. 7A is a top view of one type of stimulator element for the wrist band of FIG. 5.

The stimulator segment 502 of the wrist band 500 shall now be described in more detail with further reference to FIGS. 7A and 7B. FIG. 7A shows a top view of stimulator element 505; FIG. 7B shows a side view of element 505 at twice the scale of FIG. 7A.

Stimulator element 505 has two oppositely disposed convex protrusions, 610 and 612, joined at their respective bases by thin deformable membrane 507. As shown in FIG. 7B, the bases of protrusions 610 and 612 are coincident with planes 731 and 732 of the membrane 507.

Protrusion 610 is defined as the force-application protrusion and transmits force to protrusion 612 when the wrist band is snapped or when finger pressure is appropriately applied. Protrusion 612 is defined as the stimulus transmission protrusion and is intended to be positioned proximal to the skin surface when the wrist band is in use.

Stimulator element 505 is preferably molded or cast in one piece. The preferred material for 505 is soft silicon rubber although other flexible materials with low durometer and similar deformation properties may be specified.

The shapes of protrusions 610 and 612 are shown in the figures as hemispherical, however other shapes such as elliptical or parabolic may be alternatively specified. Further, 610 and 612 are shown as having equal size and shape. In practice however, deviations from equivalency may be tolerated. Notwithstanding, in light of the arterial, venous, and nervous system structures proximal to protrusion 612 when the wrist band is used according to this invention, pointed or sharp protrusions should be avoided.

Figure 8A:
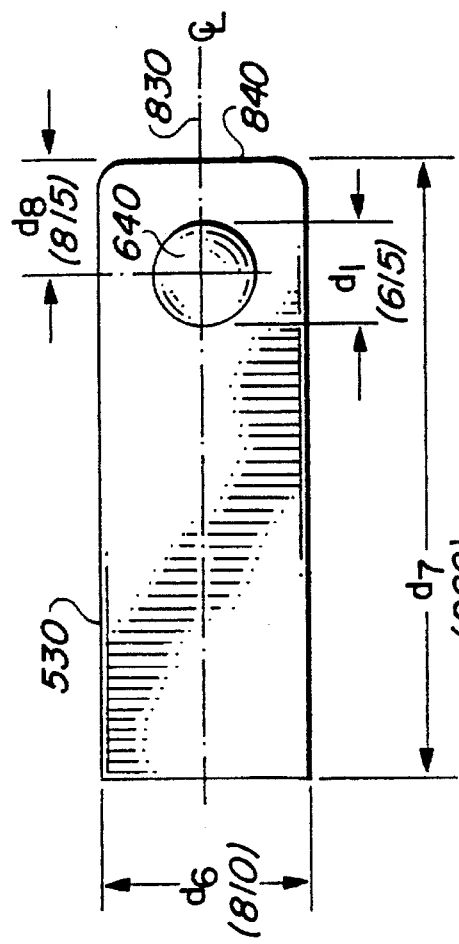
FIG. 8A is a top view of the skin-side stimulator retaining strip of the stimulator segment of the wrist band of FIG. 5.
Figure 8B:
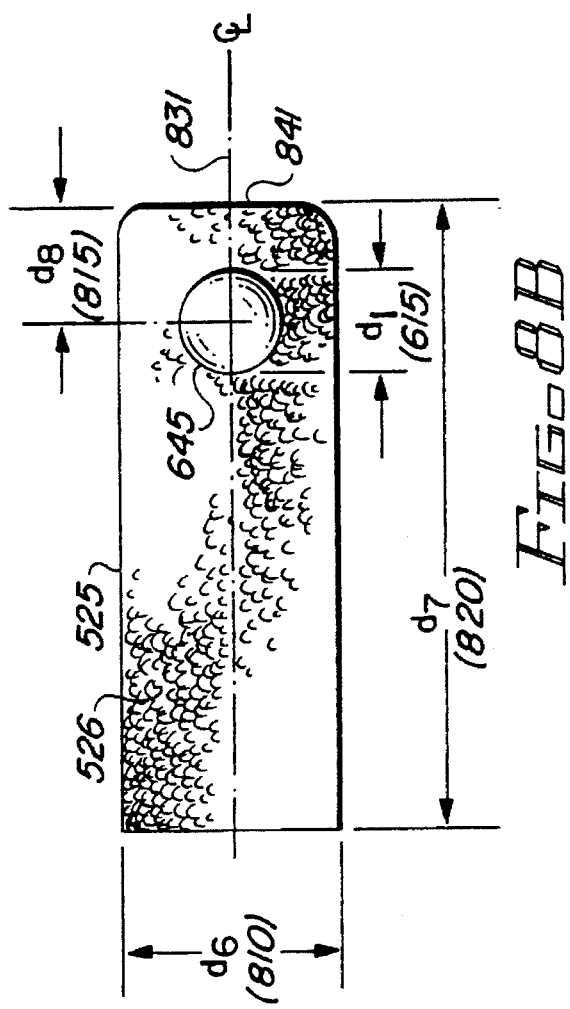
FIG. 8B is a top view of the fastening strip of the stimulator segment of the wrist band in FIG. 5.

Now consider strips 530 and 525 of stimulator segment 502. FIG. 8A shows a top view of strip 530; FIG. 8B shows a top view of strip 525 with loop-type Velcro surface 526. As shown in FIGS. 8A and 8B, strips 530 and 525 are essentially rectangular and have equal width $d_6$ (810) and equal length $d_7$ (820). To eliminate sharp corners at the skin surface when the wrist band is in use, proximal ends 840 and 841 of strips 530 and 525 have a slight, equal curvature as shown.

Strips 530 and 525 have openings 640 and 645, respectively, adjacent to proximal ends 840 and 841. Each opening is of equal diameter $d_1$ (615), the center of each opening is equidistant $d_8$ (815) from the proximal ends, and each opening is centered with respect to longitudinal center lines 830 and 831. Accordingly, if strips 530 and 525 are sandwiched with openings 640 and 645 and longitudinal center lines 830 and 831 aligned, strip 530 will exactly overlie strip 525.

By reference to FIGS. 7A, 7B, 8A, and 8B, now consider that stimulator element 505 (FIG. 7A) is sandwiched between retaining strip 530 and fastening strip 525 such that 1) the center of protrusions 612 and 610 in side view is concentric with the center of openings 640 and 645, 2) strips 530 and 525 are exactly overlapped, and 3) the longitudinal center line 730 of 505 is coincident with the longitudinal center line 830 of 530.

The desired conditions of this sandwich are that: 1) membrane 507 (FIG. 6) does not extend beyond the edges of strips 530 and 525; 2) the circumferential extent of the membrane 507 is greater than the diameter 615 of the openings in strips 530 and 525; 3) the diameter of the openings is greater than the diameter 715 of the base of protrusions 612 and 610 such that a deformation area between the edge of the openings and the edge of the protrusions attains, and 4) an attachment region exists at the periphery of the membrane 507 such that the membrane can be fastened adjacent to the periphery of the proximal end of strips 530 and 525. Necessary conditions for this to obtain are:

(a) The width $d_6$ (810) of strips 530 and 525 must be greater than the width $d_5$ (708) of membrane 507;

(b) membrane width $d_5$ (708) must be greater than the diameter $d_1$ (615) of openings 640 and 645 and $d_1$ must be greater than the diameter $d_2$ (715) of the base of protrusions 612 and 610;

(c) the distance $d_8$ (815) from the center of openings 640 and 645 to the edges 840 and 841 of strips 530 and 525 must be greater than the distance $d_3$ (707) from the center of protrusions 612 and 610 to the proximal end of membrane 507;

(d) the distance $d_4$ (705) from the center of protrusions 612 and 610 to the distal edge of membrane 507 must be equal to greater than $d_3$ (707).

FIG. 9 is a top perspective view of stimulator segment 502 of the wrist band 500 shown prior to attachment of the proximal end 521 of elastic strip 510. The view is from the skin-side aspect of the wrist band with strip 530 shown upper-most. The outline of stimulator element 505, which is sandwiched between strips 530 and 525, is shown by continuous dotted line 915. Stitching to secure the stimulator element between strips 530 and 525 is shown by broken dotted line 910. The location of stitching to attach the proximal end 521 of elastic strip 510 between strips 530 and 525 is shown by dotted line 920.

Some preferred dimensions of stimulator element 505 and strips 530 and 525 of stimulator section 502 are as follows:

From considerations based on acupuncture of the L-7 point and from anatomical considerations, a stimulator protrusion 612 with an essentially hemispherically shaped tip 723, a base diameter $d_2$ (715) of the order of 0.25" and a protrusion height 722 of 0.15"–0.25" is preferred.

The preferred diameter of the opening 640 and 645 in strips 530 and 525 is of the order of 3/8. The active area of membrane 507 will therefore be an annular ring or disk 1/16" wide surrounding the base of protrusions 612 and 610. If the stimulator element is formed in one piece from silicon rubber with a Shore-A of 35–45, a membrane thickness 720 of the order of 0.030" will
facilitate free movement of protrusions 612 and 610 when slight force is applied to either protrusion.

The width $d_6$ (810) of stimulator element strips 530 and 525 is preferably of the order of 0.75". The distance $d_8$ (815), from the center of openings 640 and 645 to the proximal end of segment 502, should be as small as practicable; this is so that when the wrist band is properly aligned over the L-7 acupuncture point, minimal overlap of segment 502 onto the dorsal aspect of the wrist will attain. The preferred distance 815 is of the order of 0.40".

As shown in FIG. 9, stimulator element 505 overlaps stitching 910. Preferably, stitching should be 0.10" proximal to the edge of strips 530 and 525 or slightly less. This being the case, the width $d_5$ (708) of stimulator element 505 should preferably be 0.65"–0.70", and the distance ds (707) from the center of protrusions 612 and 610 to the proximal edge of element 505 should preferably be 0.35"–0.38".

If it is desired (primarily for cosmetic reasons) to have the stitching closer than 0.10" to the edges of strips 530 and 525, an alternative means of securing 505 mesial to strips 530 and 525 would be to use adhesive means rather than relying on stitching.

Stimulus transmission protrusion 612 is shown in FIG. 6 as extending slightly beyond surface 535 of strip 530, and force application protrusion 610 is shown as extending slightly above surface 526 of strip 525. If the thickness of each of the strips 530 and 525 is taken to be approximately 0.15" (655 and 650 in FIG. 6), then protrusions 612 and 610 can lie either flush with surfaces 535 and 526, respectively, or can lie slightly beyond as depicted in FIG. 6. In either case, since strips 530 and 525 are stiffer than membrane 507, the effect of placing surface 535 against the skin will be to cause the tip of stimulus transmission protrusion 612 to assume an essentially flush aspect with respect to surface 535. Thus, with no force applied to protrusion 610, no stimulation of the L-7 region (via protrusion 612) will result. This is a highly desirable feature of this embodiment.

Figure 10:
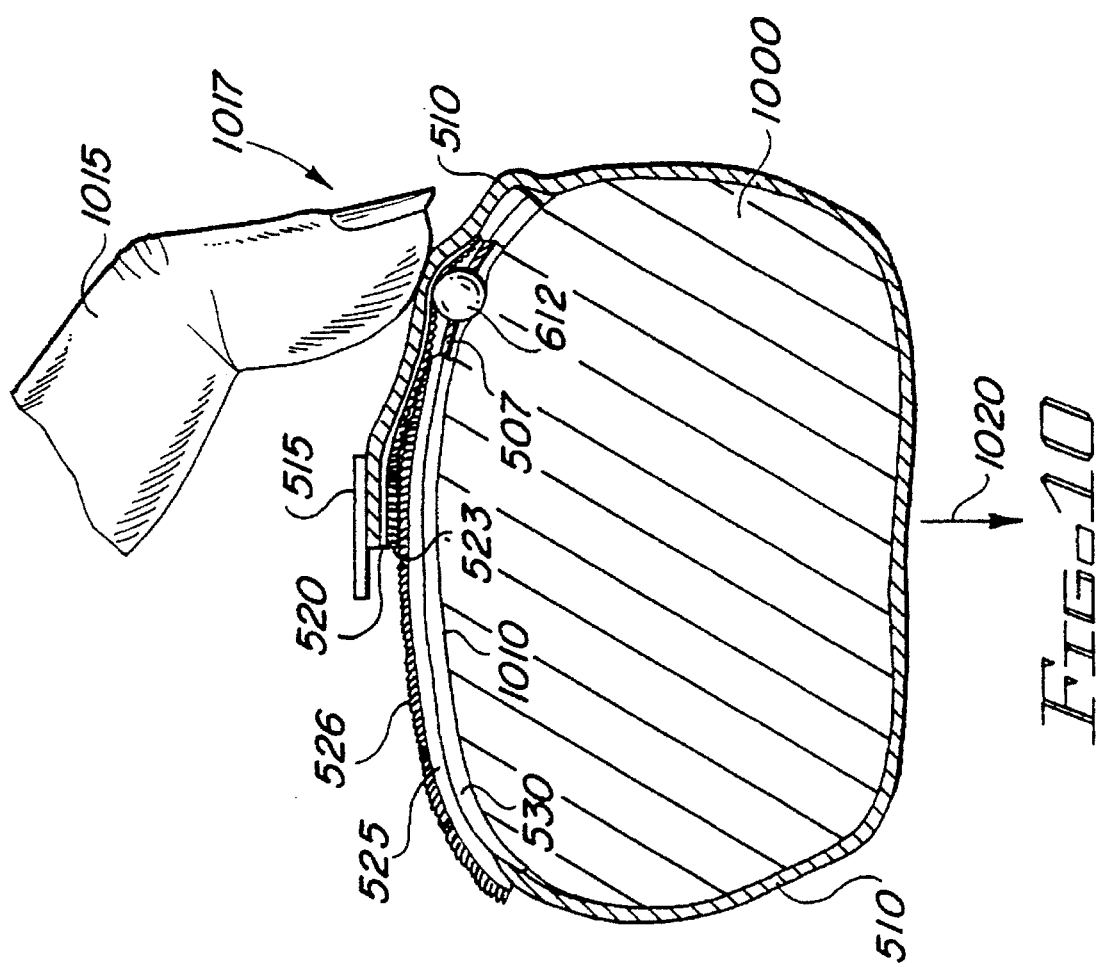
FIG. 10 is an idealized cross-sectional view of the right wrist facing toward the hand and proximally distal to the wrist crease, with the underside of the wrist uppermost, showing the wrist band of FIG. 5 in place with, and the stimulator protrusion over, the acupuncture point L-7.

The advantages of the embodiment in FIGS. 5–9 over the embodiment of FIGS. 1–4 will be better understood by reference to FIG. 10, which shows an idealized cross-sectional view of the right wrist facing toward the hand, with the underside of the wrist uppermost, with the band 500 in place, and with stimulator protrusion 612 proximal to the L-7 acupuncture point.

The wrist band of FIG. 5 is applied by first positioning the skin-side 530 of stimulator segment 502 against the underside 1010 of the wrist such that stimulator protrusion 612 is over the L-7 acupuncture point and the proximal end of segment 502 is over the radius bone (not shown) of the forearm. Elastic segment 503 (elastic strip 510) is then loosely wound around the wrist until the Velcro hook surface 523 of fastening strip 520 meshes with the Velcro loop surface 526 of strip 525. The wrist band should be adjusted so that it is just tight enough to avoid appreciable shifting of the stimulator element over the L-7 region.

It is important to note that the length $d_7$ (820 in FIG. 8) of stimulator segment 502 should be chosen such that segment 502 is slightly less than a pre-determined percentage of the distribution of under-wrist width measurements of a target user sub-population, where the measurements are taken adjacent and distal to the wrist crease. Similarly, the length of elastic segment 503 should be chosen based on accommodating a predetermined percentage of wrist circumferences in the target user sub-population.

For the target user sub-population, elastic strip 510 should overlap opening $d_1$ (640 and 645 in FIG. 6), and segment 504 of the wrist band should overlap Velcro loop surface 526 without extending appreciably beyond the underside of the wrist.

Requiring that stimulator segment 502 and wrist attachment segment 504 fall predominantly on the underside of the wrist is important in terms of user comfort and wearability of the wrist band. Additionally, requiring that the elastic strap 510, rather than the wrist attachment segment 504, overlaps openings 640, 645 will make stimulator element 505 more responsive to finger pressure and purposeful distension of the wrist band while minimizing (or eliminating) the force against L-7 when the band is simply being worn.

To accommodate variations in wrist measurements within a given user sub-population, the length of wrist attachment segment 504 should be made correspondingly less than the length of stimulator segment 502, subject to a minimum length based on Velcro shear considerations. The minimum number of wrist band sizes necessary to accommodate a target user sub-population can then be determined by analysis of appropriate anthropometric data.

As shown in FIG. 10, one method of stimulating the L-7 acupuncture point is to apply gentle finger pressure in the nominal direction 1017 shown; alternatively, finger 1015 can slowly rotate while force is being applied, thereby providing a horizontal force component in addition to the vertical force component in direction 1017. Note that due to the action of membrane 507, finger 1015 can apply directional, concentrated force to the L-7 region. Further, due to the extensibility of membrane 507, a certain amount of error in proper positioning of stimulator protrusion 612 over the desired acupuncture point can be compensated. This is another distinct advantage of the wrist band 500 configuration.

Now assume that finger 1015 is withdrawn from the wrist band. Protrusions 612 and 610 will subsequently tend to float medially between strips 530 and 525 with the tip of protrusion 612 essentially flush with the non-indented skin surface of the wrist; this minimizes or eliminates any stimulation by protrusion 612 to the L-7 region. This advantage of the invention eliminates potential deleterious effects of long term constant stimulation in the L-7 region. (Since the L-7 point is proximal to the radial artery, various blood vessels, and nerves, such stimulation might become uncomfortable for certain users and therefore preclude the continuing use of the wrist band by the withdrawing smoker.)

A second way of stimulating the L-7 region is to pull the wrist band away from the dorsal aspect of the wrist in direction 1020. This is equivalent to the method shown in FIG. 4 and provides behavioral modification benefits as well as differential acupuncture stimulation.

Another feature of the invention relates to the advantage of opposing protrusions in stimulator element 505 over a stimulator element with a single protrusion. For purpose of comparison, FIG. 7E shows a side view of a stimulator element 765 with a single stimulus transmission protrusion, 770, and no force transmission protrusion.

Consider that the width 775 of the base of protrusion 770 is equal to the width 722 of protrusion 612 (FIG. 7B); the height 780 of 770 above membrane 790 is equal to the height 722 of 612; and that membrane 790 is equivalent to membrane 507.

Figure 7C:
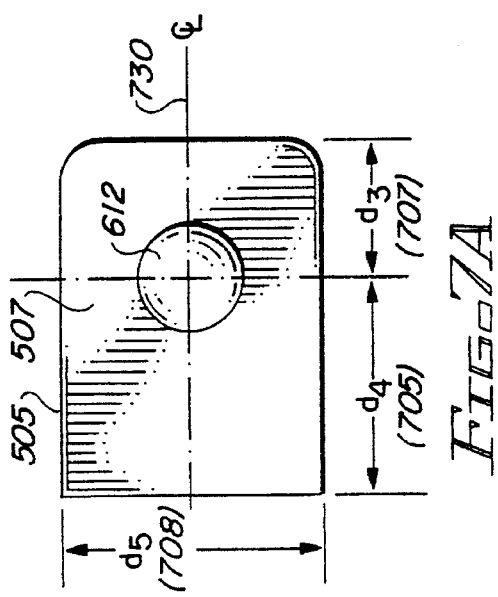
FIG. 7C is a top view of another type of stimulator element devised so that the stimulator protrusions may be permanently removed from the wrist band by a user.
Figure 7E:
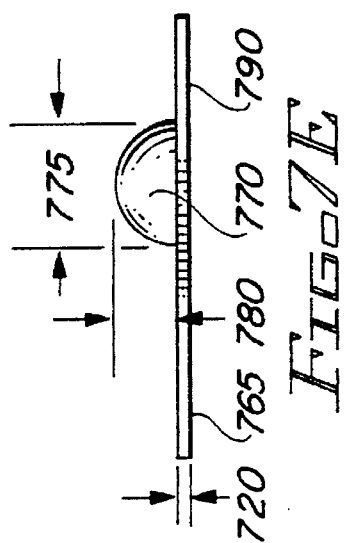
FIG. 7E is a side view of a single protrusion stimulator element, shown at the same scale as in FIG. 7A, and with perimeter equivalent to element 505 in FIG. 7A.

Now consider that in FIG. 10, stimulator element 507 (FIG. 7B) is replaced with single-protrusion stimulator element 765 (FIG. 7E). It can be appreciated that finger pressure applied to the wrist band in direction 1017 would be distributed over the entire exposed area of membrane 790 rather than directly to protrusion 610 as with stimulator element 505. Thus the double protrusion of 505 provides a more controllable concentration of force than the single protrusion element 765 when force is applied by the finger.

In the second mode of operation, when the band is pulled in direction 1020, the double protrusions of 505 will tend to provide more stimulation than the single protrusion of 765. This is due to the elastic segment 504 of the band slidably transmitting differentially more force to protrusions 610, 505 than to membranes 790, 565.

An alternative version of stimulator element 505 shall now be described. This alternative version comprises modifications to the stimulator element to make the stimulator protrusions permanently removable by the user after withdrawal from physical dependency is complete. After removal of the stimulator protrusions, the wrist band will then function solely as a behavioral modifier and can be used for a number of months or until the psychological and/or habitual factors associated with smoking have subsided.

Removal of the stimulator protrusions can be of value for several reasons. First, acupuncture has been used for treating smoking primarily during the physical withdrawal period of cessation. Secondly, in acupuncture, the L-7 (Lieque) point is a connecting point on the lung channel and has been used in treating coughing, headaches, and respiratory related complaints which exist in a number of addicted smokers; these tend to subside after the initial stage of withdrawal. Thirdly, giving the smoker a self-mediated affirmation that he has successfully completed the first stage of recovery can potentially reduce recidivism.

The alternative version shall be described with reference to FIGS. 7C and 7D. FIG. 7C is a top view of removable stimulator element 745; FIG. 7D is a side sectional view of the stimulator element in FIG. 7C at twice scale and with the thickness of the membranes further exaggerated.

Stimulator element 745 (FIG. 7C) differs from stimulator element 505 (FIG. 7A) in that a deformable membrane portion 750 and a detachment membrane portion 755 are defined. On the other hand, dimensions 705, 707, 708, 715, and 722 are identical for the two stimulator-element versions. Stimulator element 745 is preferably molded or cast in one piece using the equivalent material preferable for element 505.

The deformable membrane portion of stimulator element 745 consists of an annular ring 750, medial to protrusions 610 and 612 with thickness 762 and outside diameter $d_9$ (760). Thickness 762 is preferably identical to thickness 720 of membrane 507 (approximately 0.030").

Let a detachment membrane 755 of uniform thickness 764 be defined in the region from the circumferential outer boundary of ring 750 to the continuous outside edge of element 745. At the boundary of ring 750 and membrane 755, diameter $d_9$ is chosen such that it is greater than the diameter of openings 640, 645 in FIG. 8A, and such that the active part of membrane 750 falls within the inside boundary of stitching 915 (see FIG. 9) when the stimulator segment of the wrist band is assembled. It follows that detachment membrane 755 is stitched between strips 530 and 525 during assembly.

The thickness of membrane 755 is shown in FIG. 7D as being less than that of ring 750. The actual thickness 764 of membrane 755 is chosen so that when permanent removal of the protrusions 610, 612 is desired, a blunt tool (such as the eraser portion of a lead pencil) can be used to push the deformable membrane and stimulator protrusions through openings 640, 645 until membrane detachment is achieved. If the thickness 764 relative to thickness 762 is properly chosen, the deformable membrane portion will separate from the detachment membrane portion at the circumferential boundary of the two membranes. Clearly the force required to accomplish this should be greater than normally exerted during use of the wrist band and yet not so great as to make removal difficult.

While not shown, other alternative designs to make the stimulator protrusions removable can be considered. Among these, the uniformly thick membrane 507 shown in FIG. 7A could be molded with a sharply defined, triangularly shaped annular depression of diameter 760 and of sufficient depth relative to thickness 720 so as to act as a detachment region.

Although there have been shown and described hereinabove specific embodiments of a wrist band in accordance with the invention for the purpose of illustrating the manner in which the invention may be used to advantage, it will be appreciated that the invention is not limited thereto. Accordingly, any and all modifications, variations, or equivalent devices which may occur to those skilled in the art should be considered to be within the scope of the invention as defined in the annexed claims.

As one example, by removing acupressure stimulator 110 in the first embodiment of the wrist band 100, or stimulator element 745 in the second embodiment of the wrist band 500, the wrist band can be used strictly as a behavioral modification device to treat other non-desirable behaviors.

As a second example, it should be noted that while wrist attachment tab strip 115 facilitates the removal of the wrist band 500, the strip is not necessary for the band's proper operation; therefore, it may alternatively be removed without affecting the operational functionality of the wrist band.

As a third example, it can be noted that if diameter $d_1$ (615) of openings 640 and 645 in FIGS. 8A and 8B were made essentially equal to the diameter $d_2$ (715) of the base of protrusions 612 and 610 in FIG. 7A, the useful effects of membrane 507 would be eliminated. The resulting stimulator segment would therefore become a special case of the more general and preferred embodiments illustrated in FIGS. 5–10. Practically speaking, this modification would cause a slight amount of constant force to be exerted against the skin under protrusion 612 as a consequence of the required tautness of the wrist band to avoid slippage; this effect would be heightened if the stimulator protrusions extended appreciably beyond the retaining and fastening strips of the stimulator segment of the wrist band. Even so, if the active membrane area were removed, protrusion 610 would still afford a cue for user wrist placement and would reduce the level of constant stimulation over that of the first embodiment of the wrist band 100; such modification, while not generally recommended, might be appropriate in a more aggressive, short-term treatment regime based on stimulation of the more dorsally located "Tim Mee" acupuncture point.

Finally, the stimulator segment 502 of FIG. 9, utilizing the stimulator element of FIG. 7A, would be appropriate for differential stimulation of the P-7 Neiguan acupuncture point if the thickness of strips 530 and 525 and the protrusion height 722 were increased. This would eliminate potential problems associated with constant stimulation of P-7 in pregnant women.

What is claimed is:

1. A device for use by a person to overcome cigarette smoking addiction comprising:

a wrist band having a non-elastic stimulator segment, a non-elastic wrist attachment segment, and an elastic segment connected between said non-elastic segments;

said stimulator segment including:

a fastening strip;

a retaining strip extending along and substantially co-extensive with said fastening strip, at least one of said strips having an opening therein; and a stimulator element secured between said strips and having a rounded protrusion on at least one side thereof, said stimulator element being mounted so that said protrusion is accessible through said opening for contacting an acupuncture point on a user's wrist when the wrist band is installed thereon.

2. The device of claim 1 wherein each of said strips has an opening therein, said strips being mounted with said openings in alignment, and wherein said stimulator element comprises two oppositely disposed convex protrusions extending through respective ones of the openings in said strips.

3. The device of claim 2 wherein said stimulator element further comprises a membrane having a deformable portion extending about said protrusions so as to permit limited lateral displacement of said protrusions relative to the stimulator segment when in position on a user's wrist.

4. The device of claim 2 wherein said stimulator element further comprises a membrane having a deformable portion extending about said protrusions so as to permit limited axial displacement of said protrusions relative to the stimulator segment when in position on a user's wrist.

5. The device of claim 2 wherein said stimulator element further comprises a membrane having a rupturable portion so as to permit ready removal of said protrusions without disassembling the stimulator segment.

6. The device of claim 1 further including a tab strip attached to said fastening strip to project beyond the fastening strip to facilitate release of the fastening strip from the retaining strip for removal of the wrist band from the user's wrist.

7. The device of claim 1 wherein said band is between 0.50 and 1.0 inch wide, wherein the maximum elongation of the elastic segment when stretched without exceeding its elastic limit is not in excess of 100%, wherein the tensile force required to attain said 100% elongation is not in excess of five pounds, and wherein said fastening and retaining strips comprise respective hook and loop fasteners.

8. A device for use in acupressure therapy comprising:

a first strip;

a second strip extending along and substantially co-extensive with said first strip, at least one of said strips having an opening therein; and a stimulator element secured between said strips and having a rounded protrusion on at least one side thereof, said stimulator element being mounted so that said protrusion is accessible through said opening for contacting an acupressure point on the human body.

9. The device of claim 8 wherein each of said strips has an opening therein, said strips being mounted with said openings in alignment, and wherein said stimulator element comprises two oppositely disposed convex protrusions extending through respective ones of the openings in said strips.

10. The device of claim 9 wherein said stimulator element further comprises a membrane having a deformable portion extending about said protrusions so as to permit limited lateral displacement of said protrusions relative to the stimulator element when positioned for use in acupressure therapy.

11. The device of claim 9 wherein said stimulator element further comprises a membrane having a deformable portion extending about said protrusions so as to permit limited axial displacement of said protrusions relative to the stimulator element when positioned for use in acupressure therapy.

12. The device of claim 9 wherein said stimulator element further comprises a membrane having a rupturable portion so as to permit ready removal of said protrusions without disassembling the stimulator element.

13. A method of using a pressure application device for both acupressure and behavioral modification therapy to aid an addicted cigarette smoker in quitting smoking, which device comprises:

a wrist band having a non-elastic stimulator segment, a non-elastic wrist attachment segment, and an elastic segment connected between said non-elastic segments;

said stimulator segment including:

a fastening strip;

a retaining strip extending along and substantially co-extensive with said fastening strip, at least one of said strips having an opening therein; and a stimulator element secured between said strips and having a rounded protrusion on at least one side thereof, said stimulator element being mounted so that said protrusion is accessible through said opening for contacting an acupuncture point on a user's wrist when the wrist band is installed thereon;

said method comprising the steps of:

A. positioning said device on one of said smoker's arms in close proximity to the Lieque acupuncture point located proximal to the styloid process of the radius bone above the smoker's wrist crease;

B. wrapping said wrist band around said smoker's arm until slight pressure upon said Lieque point is felt by the smoker;

C. securing said wrist band on said smoker's arm while maintaining said slight pressure;

D. pulling said wrist band away from said arm in a direction perpendicular thereto and opposite to said wrist crease in order to provide differential stimulation to the Lieque acupuncture point when the desire to smoke arises; and E. releasing said wrist band to cause a slight, non-aversive stinging sensation when said wrist band contacts said arm as a behavioral modification strategy.

14. The method of claim 13 further including the steps of:

substituting a more compliant stimulator segment for the stimulator segment of said device; and repeating steps A through E.

15. The method of claim 13 wherein the stimulator element of said device is formed of hard plastic material and further comprising the steps of sequentially replacing the stimulator element with increasingly more compliant stimulator elements and, after each stimulator element replacement, repeatedly performing the series of steps A through E until the smoker's desire to smoke decreases.

16. The method of claim 13 further including the step of manually applying pressure to the stimulator element for a period of several seconds immediately after performing steps D and E.

17. The method of claim 13 comprising the step of manually applying pressure to the stimulator element for a period of several seconds instead of performing steps D and E.

* * * * *